United States Patent
Dunn

(10) Patent No.: US 11,666,249 B1
(45) Date of Patent: Jun. 6, 2023

(54) METHOD AND SYSTEM FOR COGNITIVE TRAINING OF THE BRAIN OF A HUMAN BODY USING CONTRALATERAL MOVEMENT

(71) Applicant: Human Performance Inc., Layton, UT (US)

(72) Inventor: Timothy Todd Dunn, Mooresville, NC (US)

(73) Assignee: HUMAN PERFORMANCE INC., Layton, UT (US)

( * ) Notice: Subject to any disclaimer, the term of this patent is extended or adjusted under 35 U.S.C. 154(b) by 0 days.

(21) Appl. No.: 17/891,553

(22) Filed: Aug. 19, 2022

(51) Int. Cl.
*A61B 5/11* (2006.01)
*A61B 5/16* (2006.01)

(52) U.S. Cl.
CPC ............ *A61B 5/1124* (2013.01); *A61B 5/162* (2013.01); *A61B 2562/0219* (2013.01)

(58) Field of Classification Search
CPC .................. A61B 5/1124; A61B 5/162; A61B 2562/0219; A63B 69/0055; A63B 24/0006; H04N 5/144; A63F 2300/6027; A63F 2300/638; A63F 13/67; A63F 13/533; A63F 13/44
See application file for complete search history.

(56) References Cited

U.S. PATENT DOCUMENTS

| | | | |
|---|---|---|---|
| 8,251,818 B1 * | 8/2012 | Dunn | A63B 69/0055 463/36 |
| 10,284,752 B1 | 5/2019 | Canfield et al. | |
| 2007/0148624 A1 * | 6/2007 | Nativ | A63B 24/0006 434/258 |

OTHER PUBLICATIONS

Xsens DOT User Manual, Document ZD0502P, Revision G, Xsens Technologies B.V., 34 pages (Jun. 2022).

\* cited by examiner

*Primary Examiner* — Patrick Fernandes
(74) *Attorney, Agent, or Firm* — Panitch Schwarze Belisario & Nadel LLP

(57) ABSTRACT

An automated method for cognitive training of the brain of a human using contralateral movement is provided wherein the body of the human is defined, in part, by having contralateral sides and the human body has a plurality of motion tracking sensors attached to respective limbs of the human body.

8 Claims, 19 Drawing Sheets

US 11,666,249 B1

METHOD AND SYSTEM FOR COGNITIVE TRAINING OF THE BRAIN OF A HUMAN BODY USING CONTRALATERAL MOVEMENT

CROSS-REFERENCE TO RELATED APPLICATIONS

This application is related to U.S. patent application Ser. No. 17/891,559 filed Aug. 19, 2022 entitled "Method for associating a plurality of wireless motion tracking sensors to respective limbs of a human body."

COPYRIGHT NOTICE AND AUTHORIZATION

Portions of the documentation in this patent document contain material that is subject to copyright protection. The copyright owner has no objection to the facsimile reproduction by anyone of the patent document or the patent disclosure as it appears in the Patent and Trademark Office file or records, but otherwise reserves all copyright rights whatsoever.

BACKGROUND OF THE INVENTION

"Contralateral" is defined as "pertaining to the other side," and is in contrast to "Ipsilateral" which is considered the opposite of contralateral and occurs on the same side. More specifically, in medicine, "contralateral" is defined as "relating to or denoting the side of the body opposite to that on which a particular structure or condition occurs," whereas ipsilateral is defined as "situated or appearing on or affecting the same side of the body."

Accordingly, "contralateral movement" pertains to exercising muscles on opposite sides of the body from one another, whereas "ipsilateral movement" pertains to exercising muscles on the same side of the body. Consider, for example, a human body that is defined, in part, by having four quadrants, one for each limb of the human body. Examples of a contralateral movement for the human body would be (i) simultaneous movement of the left hand and right hand; or (ii) simultaneous movement of the left foot and right foot. Contralateral movement also includes cross-contralateral movement such as (i) simultaneous movement of the left hand and right foot; or (ii) simultaneous movement of the right hand and left foot. Contralateral exercises, and the benefits thereof, are well-known in the art.

Current training systems exist which are designed to improve reflexes by prompting a human to make specific hand and foot movements in response to visual stimuli presented to the human on a display screen. One such system is described in U.S. Pat. No. 8,251,818 (Dunn et al.). However, this training system does not address contralateral movement.

Notwithstanding the knowledge of contralateral exercises and reflex training systems, there is an unmet need for methods and systems that train an individual (human) using contralateral movement based on movement instructions provided to the individual. The present invention fulfills such a need.

SUMMARY OF THE PRESENT INVENTION

An automated method for cognitive training of the brain of a human using contralateral movement is provided wherein the body of the human is defined, in part, by having contralateral sides and the human body has a plurality of motion tracking sensors attached to respective limbs of the human body. A method is also provided for associating a plurality of wireless motion tracking sensors attached to limbs of a human body.

BRIEF DESCRIPTION OF THE DRAWINGS

Preferred embodiments of the present invention will now be described by way of example with reference to the accompanying drawings.

DETAILED DESCRIPTION OF THE INVENTION

Figure 1A:
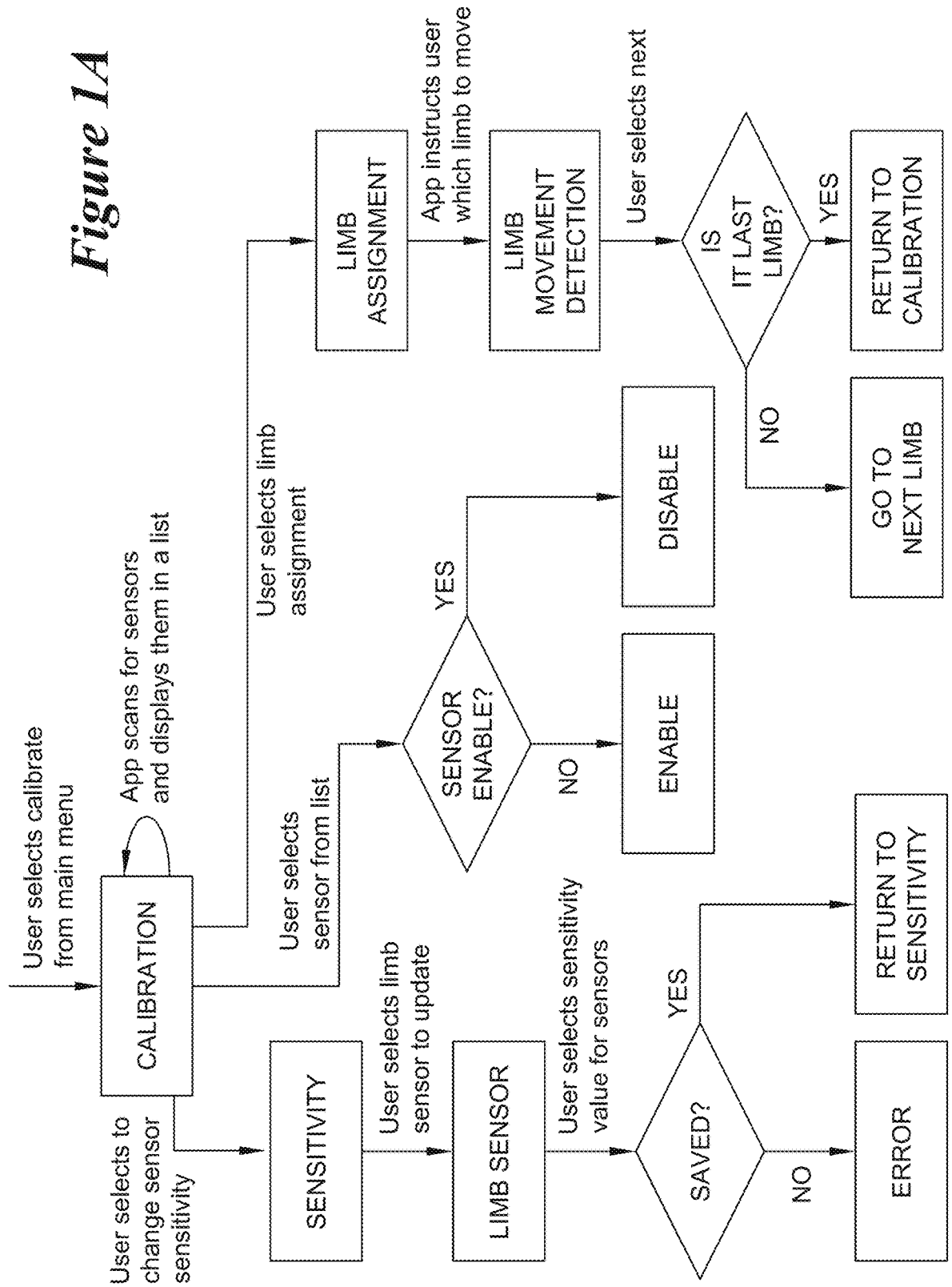
FIGS. 1A, 1B, and 1C are flowcharts in accordance with preferred embodiments of the present invention.

Certain terminology is used herein for convenience only and is not to be taken as a limitation on the present invention.

The words "a" and "an", as used in the claims and in the corresponding portions of the specification, mean "at least one."

I. Training System and Method

One preferred embodiment of the present invention provides an automated method for cognitive training of a human using contralateral movement. (The "human" is also interchangeably referred to herein as an "individual" or a "person" or a "user" or a "test subject.") The body of the human is defined, in part, by having contralateral sides. The human body has a plurality of motion tracking sensors attached to limbs of the human body. (The motion tracking sensors are also interchangeably referred to herein as "sensors" or "limb sensors.") At least two of the motion tracking sensors are connected to, and associated with, specific contralateral limbs of the human body. In one preferred embodiment, the method operates as follows:

1. A succession of human body movement instructions are displayed on a display that is in view of the human. Each human body movement instruction indicates specific limbs of the human body that should be moved in response to the display. At least some of the human body movement instructions indicate that contralateral limb movement should be made in response to the display. For example, the display may include four quadrants, one for each limb of the human body, and each limb of the human body movement instruction is associated with a respective quadrant of the display. The display may show movement instructions that are not contralateral limb movements (e.g., ipsilateral movement instructions), or that show movement of only one limb. However, at least some of the human body movement instructions indicate that contralateral limb movement should be made.

2. Record the time of initial display of each of the human body movement instructions.

3. Record limb movement of the motion tracking sensors, and detect within a measurement window at least the following information:

i. If or when the limb movement for each of the motion tracking sensors exceeds a predetermined threshold, thereby indicating a responsive limb movement. For example, a twitch of the limb will not likely satisfy the predetermined threshold unless the predetermined threshold is set to be very low. In most use cases, a twitch of the limb would not be sufficient movement to qualify as the desired amount of movement for training purposes, but there may be limited use cases where even a twitch of the limb would be sufficient movement to qualify as the desired amount of movement for the particular training purpose. The threshold is thus set to the desired level based on the training purposes.

ii. A time when the limb movement for each of the motion tracking sensors exceeds the predetermined threshold.

4. For each of the succession of human body movement instructions, perform the following functions:

i. Compare whether any responsive limb movements match the most recently displayed contralateral limb movement instruction for the same limbs.

ii. Detect whether any responsive limb movement occurred only after the contralateral limb movement instructions were displayed using the recorded time in step 2 and the detected time in step 3*ii*.

5. Record whether there is a correct or incorrect match of the contralateral limbs that should have been moved based on the contralateral limb movement instructions and the recorded and detected times.

6. Calculate reaction time of the human to each of the contralateral limb movement instructions using the time of initial display of each of the human body movement instruction and the time that the corresponding limbs in the limb movement instructions are detected by their respective motion tracking sensors as exceeding the predetermined threshold.

In one preferred embodiment, the human body movement instruction includes directional movement instructions, and the motion tracking sensors include directional movement detection. In this embodiment step 4 will include the following additional function:

iii. Compare whether any responsive limb movements match the most recently displayed contralateral limb movement instruction for the same limbs with respect to the instructed directional movement.

Similarly, in this embodiment wherein the human body movement instruction includes directional movement instructions, step 5 will record whether there is a correct or incorrect match of the contralateral limbs that should have been moved based on the contralateral limb movement instructions with respect to the instructed directional movement.

Various outcomes may occur based on the movement detection. To provide a real-world example, these outcomes will presume that the predetermined threshold to be detected as being a "responsive limb movement" is a limb movement of at least 6 inches and that the measurement window is 3 sec. That is, a limb must be moved at least 6 inches from its location at the time of initial display of a human body movement instruction. The measurement window begins at the time of the initial display of the human body movement instruction and ends 3 sec later in this example. Of course, the predetermined threshold will depend entirely upon the particular training that the person is undergoing. Examples of various scenarios and results are provided below using the 6 inch value, wherein all outcomes occur within the 3 sec measurement window):

Scenario 1a: The human body movement has instructed the person to move their left arm and right foot. The person moved their left arm 6 inches by 0.3 sec and moved their right foot 6 inches by 0.5 sec, and thus responsive limb movements were detected for the left arm and right foot. The person did not move their right arm or left foot by any discernible distance, and thus no responsive limb movement was made by the right arm or left foot. Note that the person could also have moved their left arm or right foot by distances more than 6 inches within the measurement window and the result would have still been the same, namely, that responsive limb movements would have been detected by the left arm and right foot. Likewise, the person could also have moved their right arm or left foot by discernible distances which are less than 6 inches within the measurement window and the result would also have still been the same, namely, that no responsive limb movement was made by the right arm or left foot.

Result for 1a: Correct match of contralateral limb movement

Scenario 1b: The human body movement has instructed the person to move their left arm and right foot (same instructions as scenario 1a). The person moved their left arm 6 inches by 0.3 sec but only moved their right foot 4 inches by 3 sec. which is the end of the measurement window. Thus, responsive limb movements were detected for only the left arm. The right arm and left foot movements were the same as in scenario 1a.

Result for 1b: Incorrect match of contralateral limb movement

Scenario 1c. The human body movement has instructed the person to move their left arm and right foot (same instructions as scenario 1a). The person moved their left arm 6 inches after 0.3 sec and moved their left foot 6 inches at 0.5 sec, and thus responsive limb movements were detected for the left arm and left foot. The person did not move their right arm or right foot by any discernible distance, and thus no responsive limb movement was made by the right arm or right foot.

Result for 1c: Incorrect match of contralateral limb movement

As part of the training process, some of the displayed human body movement instructions will not be contralateral movement instructions. Thus, contralateral movement instructions may be mixed together with ipsilateral movement instructions, or with single limb movement instructions. However, the focus of one preferred embodiment of the present invention is only on whether or not the person correctly responded to contralateral movement instructions.

In addition to determining whether or not the person correctly responded to contralateral movement instructions, it is also desirable to calculate reaction time of the person to each of the contralateral limb movement instructions. As explained above, the reaction time may be determined using the time of initial display of each of the human body movement instruction and the time that the corresponding limbs in the limb movement instructions are detected by their respective motion tracking sensors as exceeding the predetermined threshold, and thereby indicating a responsive limb movement. In Scenario 1a, the reaction time is 0.5 sec, which is the time in which both contralateral limb movements were detected as having been made.

As discussed above, in one preferred embodiment, the human body movement instruction includes directional movement instructions, and the motion tracking sensors include directional movement detection. In one implementation, the motion tracking sensor may be a sensor that can detect movement in three directions, such as the Xsens DOT sensor commercially available from Xsens Technologies B.V. In this embodiment, the respective limbs must not only exhibit motion data that exceeds a predetermined threshold, thereby indicating a responsive limb movement, but the movement must be in the same direction as indicated on the display. For example, if the human body movement has instructed the person to move their left arm forward and their right foot backward, a correct match would require the limb movements to mimic these directions. If either one of the limbs did not move in the appropriate direction, such as by moving sideways or opposite to the desired direction, then there would be an incorrect match of contralateral limb movement, even though the respective limb was moved by an amount that exceeded the predetermined threshold.

II. Limb Assignment to Respective Motion Tracking Sensors

To perform the training method and system described in section I above, it is necessary to assign or associate a motion tracking sensor to respective limbs of the human body. Accordingly, in another preferred embodiment of the present invention, a method is provided for associating a plurality of wireless motion tracking sensors attached to limbs of a human body of a human. Each motion tracking sensor is attached to one of the respective limbs of the human. For example, the motion tracking sensors may be attached to left and right wrists and left and right ankles of the human. Each motion tracking sensor has a unique identifier. Each motion tracking sensor transmits motion data and its unique identifier to a nearby receiving device when placed in an active state. In operation, the method operates as follows:

1. A database stores at least the following data (information) for each motion tracking sensor that is placed in an active state and which is detected by the receiving device:
   i. The unique identifier of the motion tracking sensor.
   ii. A specific limb that that the motion tracking sensor is associated with, wherein the specific limb is initially unassigned when detected by the receiving device.
2. The receiving device detects the unique identifiers of each of the motion tracking sensors and stores the unique identifiers in the database.
3. A display that is in view of the human displays a human body movement instruction indicating a specific limb of the human body that should be moved in response to the display. In one example, the human body movement instruction is an instruction to shake one of the limbs of the human, the shaking being the detected motion data.
4. The receiving device detects limb movement from one of the motion tracking sensors by detecting motion data that exceeds a predetermined threshold, thereby indicating a responsive limb movement.
5. The specific limb of the human body that was indicated should be moved in response to the display is associated with the motion tracking sensor that was detected as having the responsive limb movement.
6. The database is updated to assign the motion tracking sensor to the specific limb that was detected as having the responsive limb movement.
7. Steps 3-6 are repeated for the remaining limbs of the human body, thereby associating each of the motion tracking sensors with a respective one of the limbs of the human body.

In one preferred embodiment, the receiving device detects limb movement from one of the motion tracking sensors only when motion data that exceeds a predetermined threshold is received from only a single motion tracking sensor. In this manner, if the human inadvertently moves two different limbs at the same time, the motion data will be ignored. The human may be prompted to repeat the process for the limb that was attempting to be assigned, and optionally, a message may be included in the display to communicate to the human that the other limbs should remain as stationary as possible.

III. Detailed Disclosure of Training System/Method and Limb Assignment

The detailed disclosure is described in the context of application software (app). The app may execute on a portable device (e.g., an iPad®) or on a desktop computer.

Figure 1B:
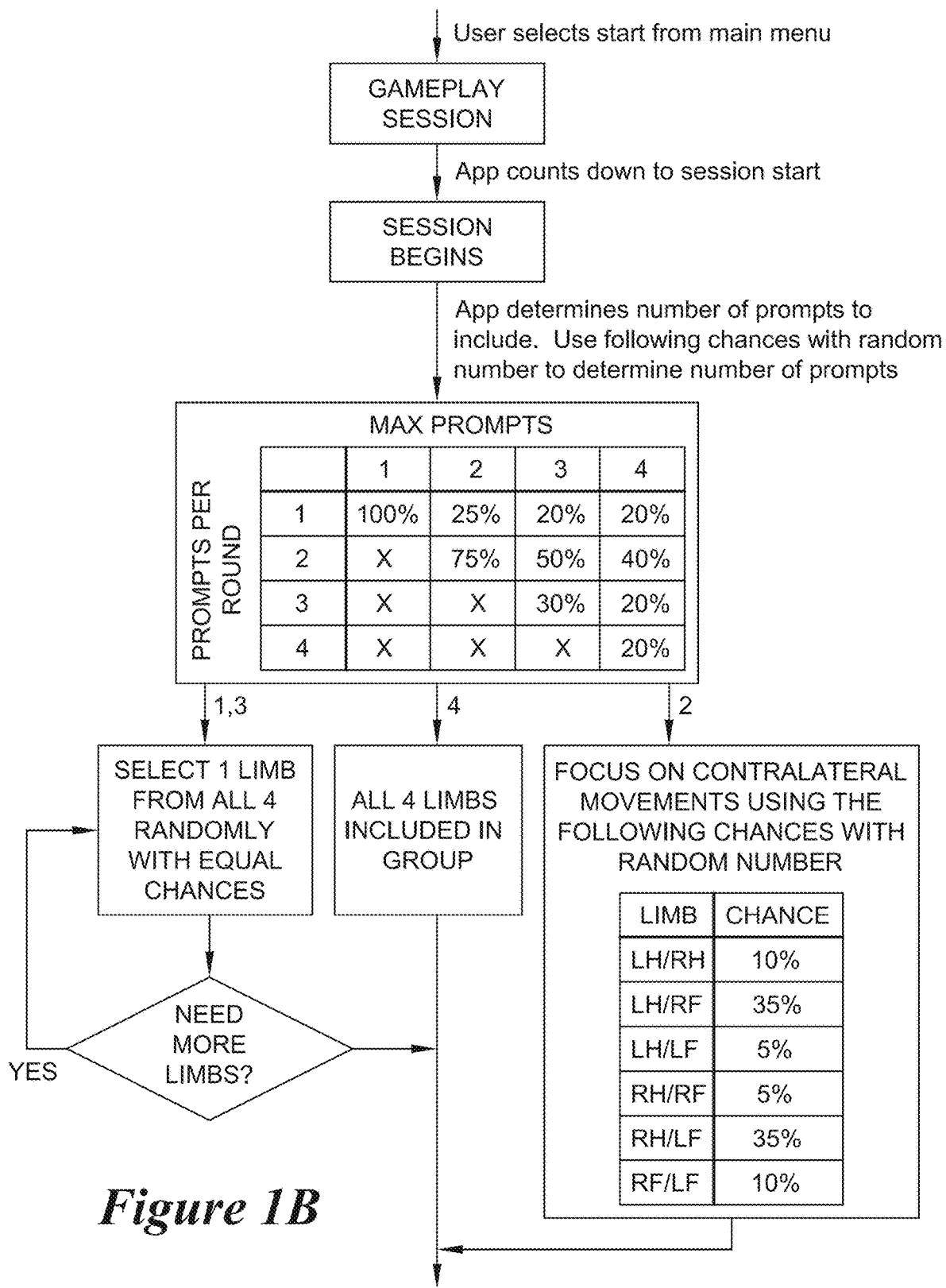
Figure 1C:
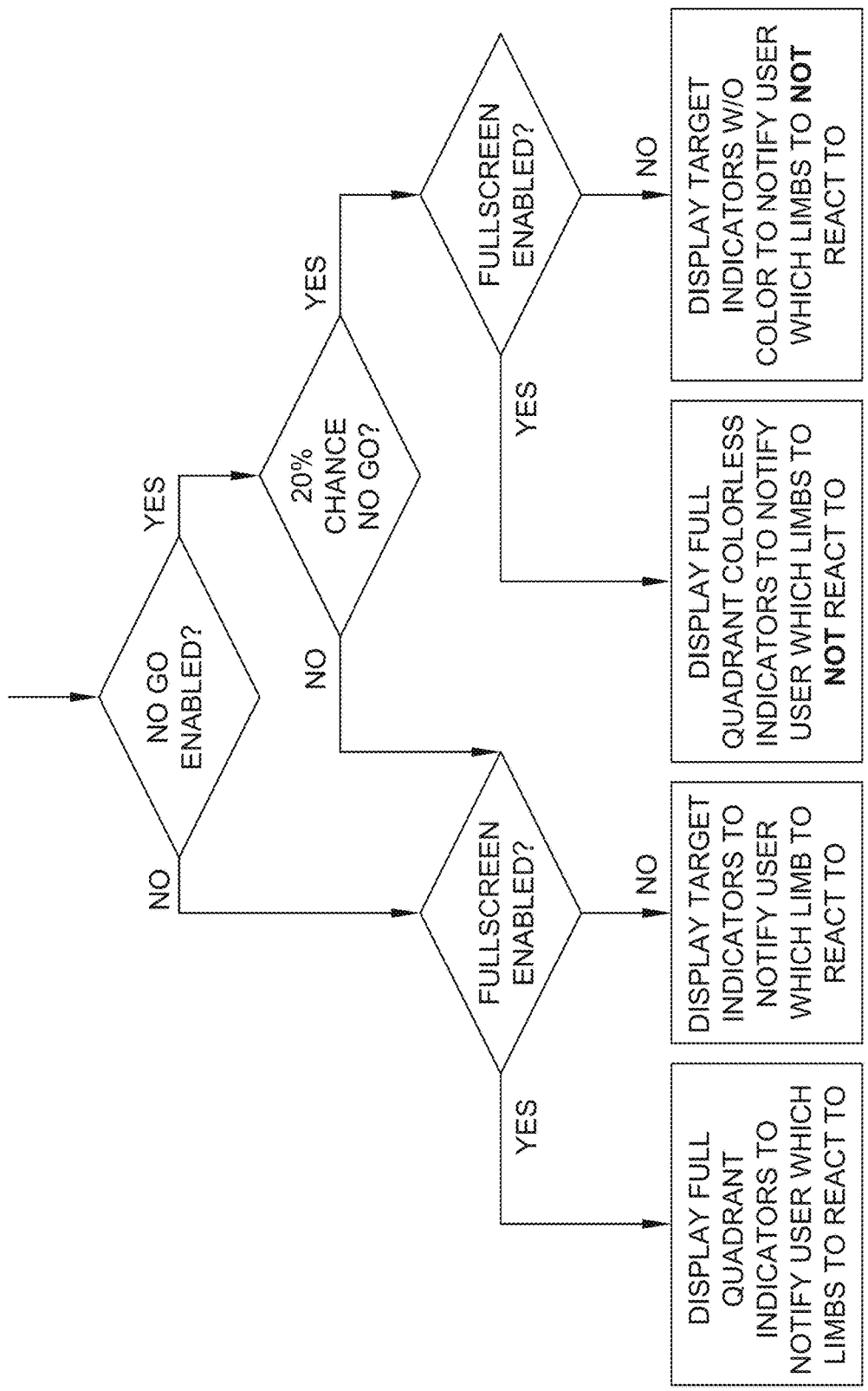

FIGS. 1A, 1B, and 1C are flowcharts in accordance with preferred embodiments of the present invention. FIG. 1A is a flowchart of the limb assignment process, and FIGS. 1B and 1C, taken together, is a flowchart of a limb selection process for the training method.

Referring to FIG. 1A, the limb assignment steps are related to FIGS. 2D-2G which are discussed below. The sensitivity steps are used to adjust the sensitivity of the limb sensors. The sensitivity is further described in the pseudocode below.

FIG. 1B illustrates a table that is used to determine the number of prompts and the frequency distribution of prompts per round. Here, the number of prompts refers to the number of limbs that are presented on the display screen for the person to react to. Thus, when max prompt=2, no more than two limbs at a time are presented on the display screen for the person to react to. When the max prompt=2, the prompts per round will have a distribution of 1 prompt (1 limb) 25% of the time, and 2 prompts (2 limbs) 75% of the time. When only one prompt is displayed, no contralateral movement should occur. However, it may still be valuable to include one limb prompts in the training process. When two prompts are displayed, the prompts may or may not indicate contralateral movement. For example, a left hand/left foot combination (LH/LF) is not a contralateral movement, whereas a left hand/right foot combination (LH/RF) is a contralateral movement.

When two prompts are displayed, FIG. 1B also illustrates a table that shows sample percentages that may be used for displaying each one of different two limb movement combinations (e.g., LH/RH combination will appear 10% of the time, LH/RF combination will appear 35% of the time, and so on). In this table, the only prompts that are not contralateral movements are LH/LF and RH/RF.

Figure 2H:
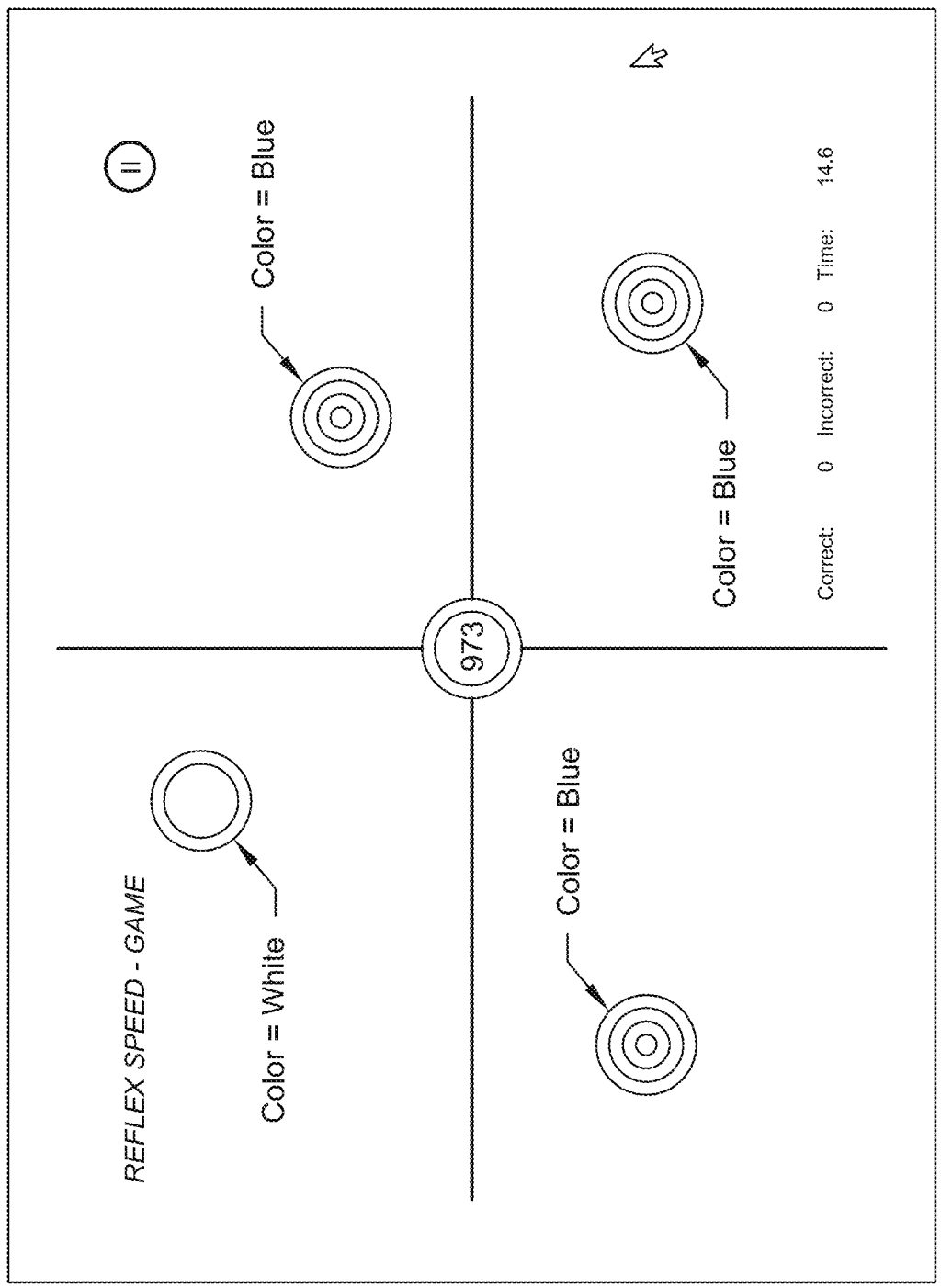
Figure 3:
FIG. 3 shows a test setup with a user interface display screen and a human reacting to an action requested to be performed.

Three limbs may be shown when max prompt=3 or max prompt=4. For example, FIG. 2H and FIG. 3 show instructions to move three limbs, so in these are examples, max prompt=3 or 4. When three limbs are shown, only two of them are associated with "contralateral movement." In these three limb instructions, if the person correctly moves all three limbs, this is considered to be a correct match of the contralateral limbs. Furthermore, if the person correctly moves the contralateral limbs but does not respond correctly to the third limb, this is still considered to be a correct match of the contralateral limbs.

FIG. 1C also shows an option to enable a "NO-GO" display feature which is discussed below with respect to FIG. 2H. In one preferred embodiment, 20% of the indicia are NO-GO indicia. The lack of a display of any indicia is equivalent to the NO-GO indicia in that the person should not respond with any limb movement for that particular limb. Another option is to enable a full-screen version of the display which displays full quadrant indicators, also referred to herein as "solid-colored rectangular indicia." Otherwise, only target indicators, also referred to herein as "circle indicia," are shown.

Figure 2A:
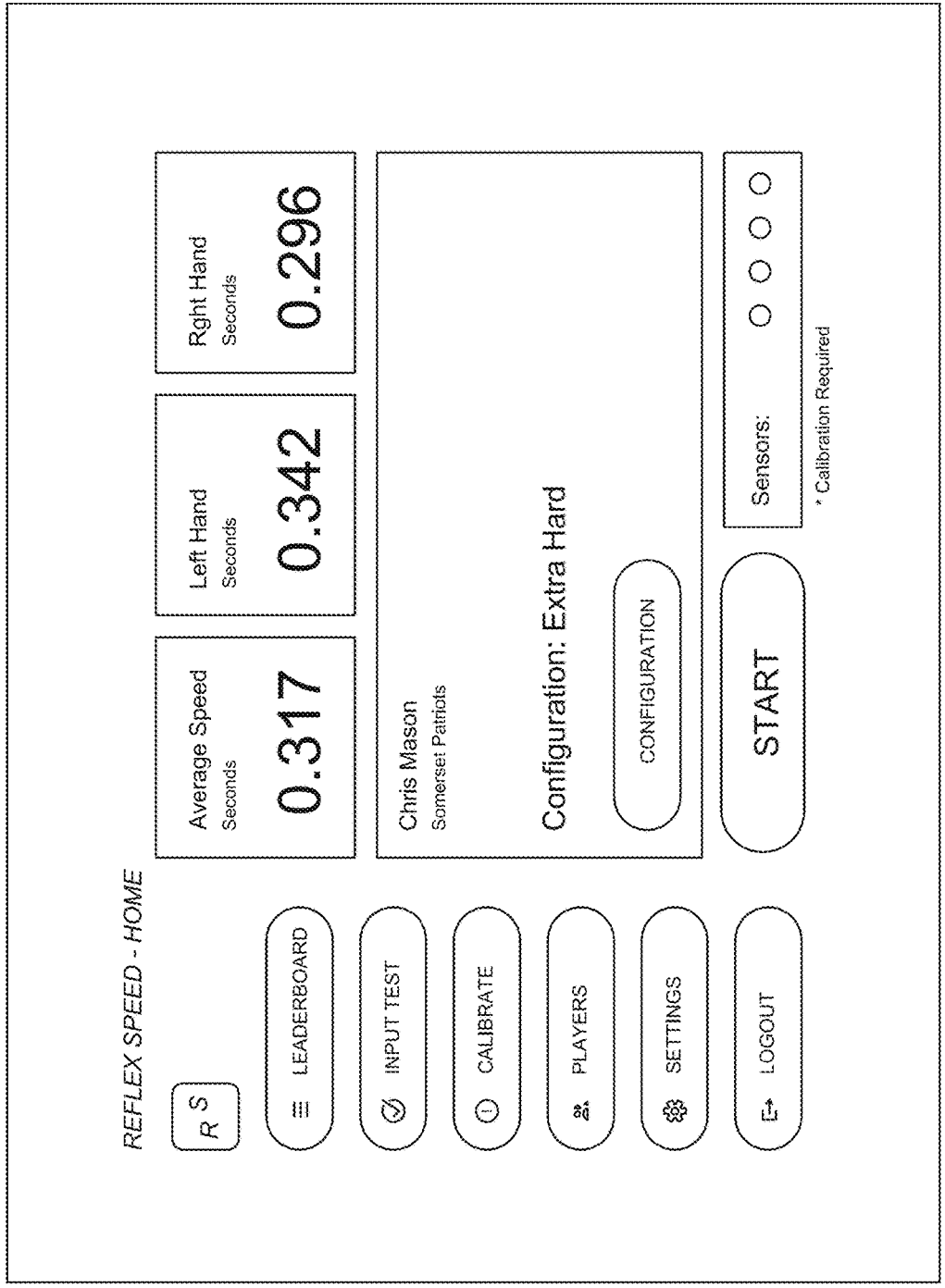
FIGS. 2A-2N show user interface display screens for implementing preferred embodiments of the present invention.
Figure 2B:
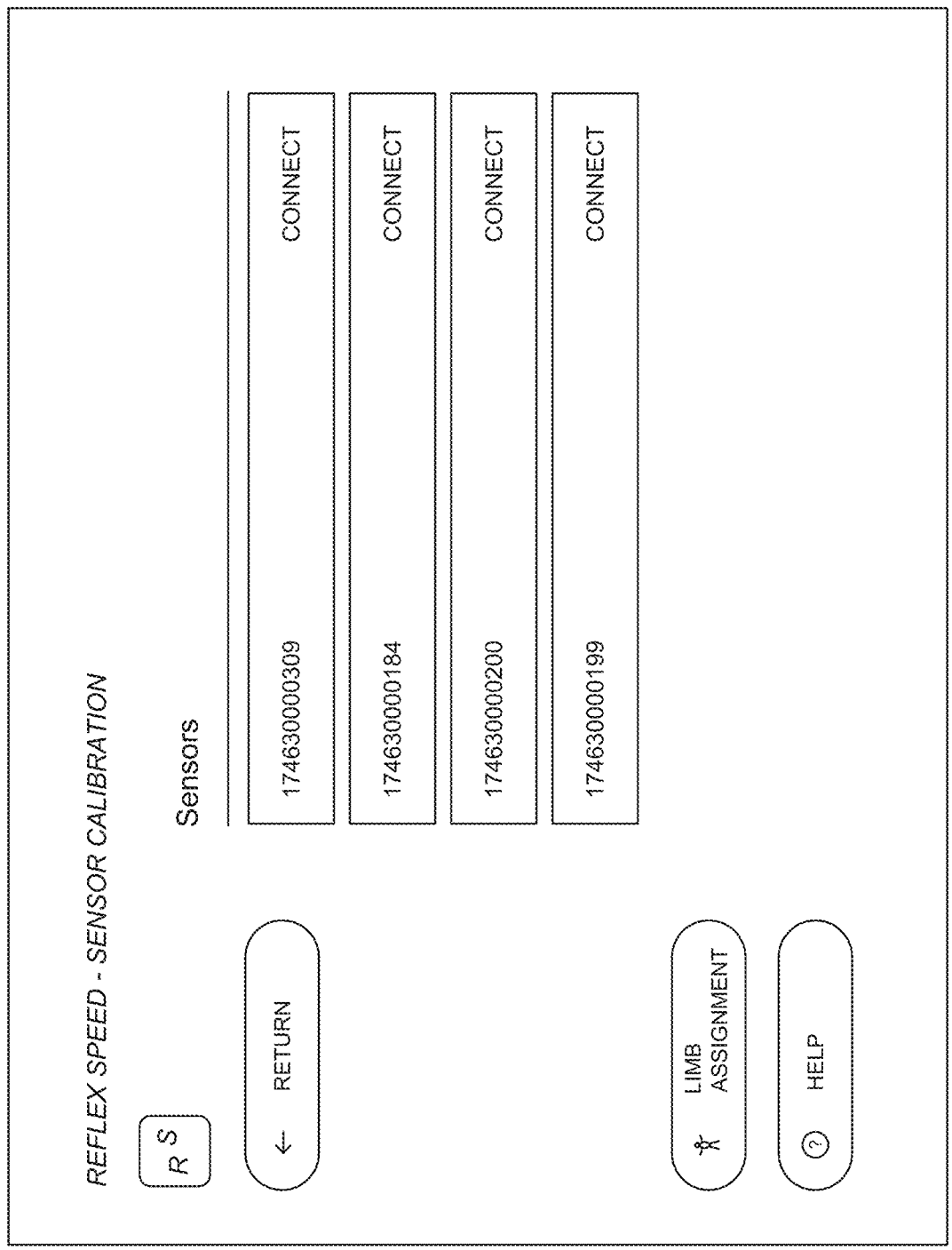
Figure 2C:
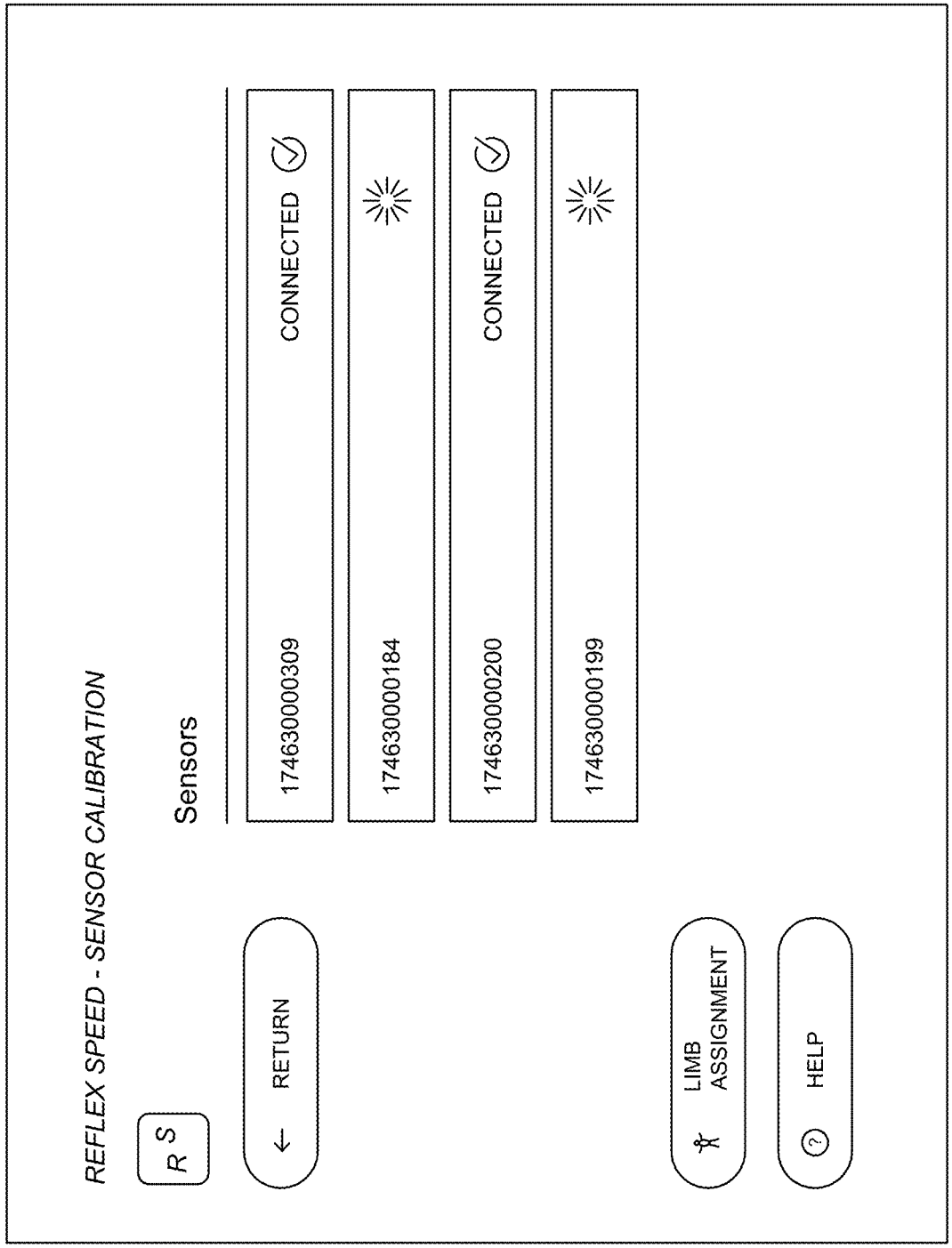
Figure 2D:
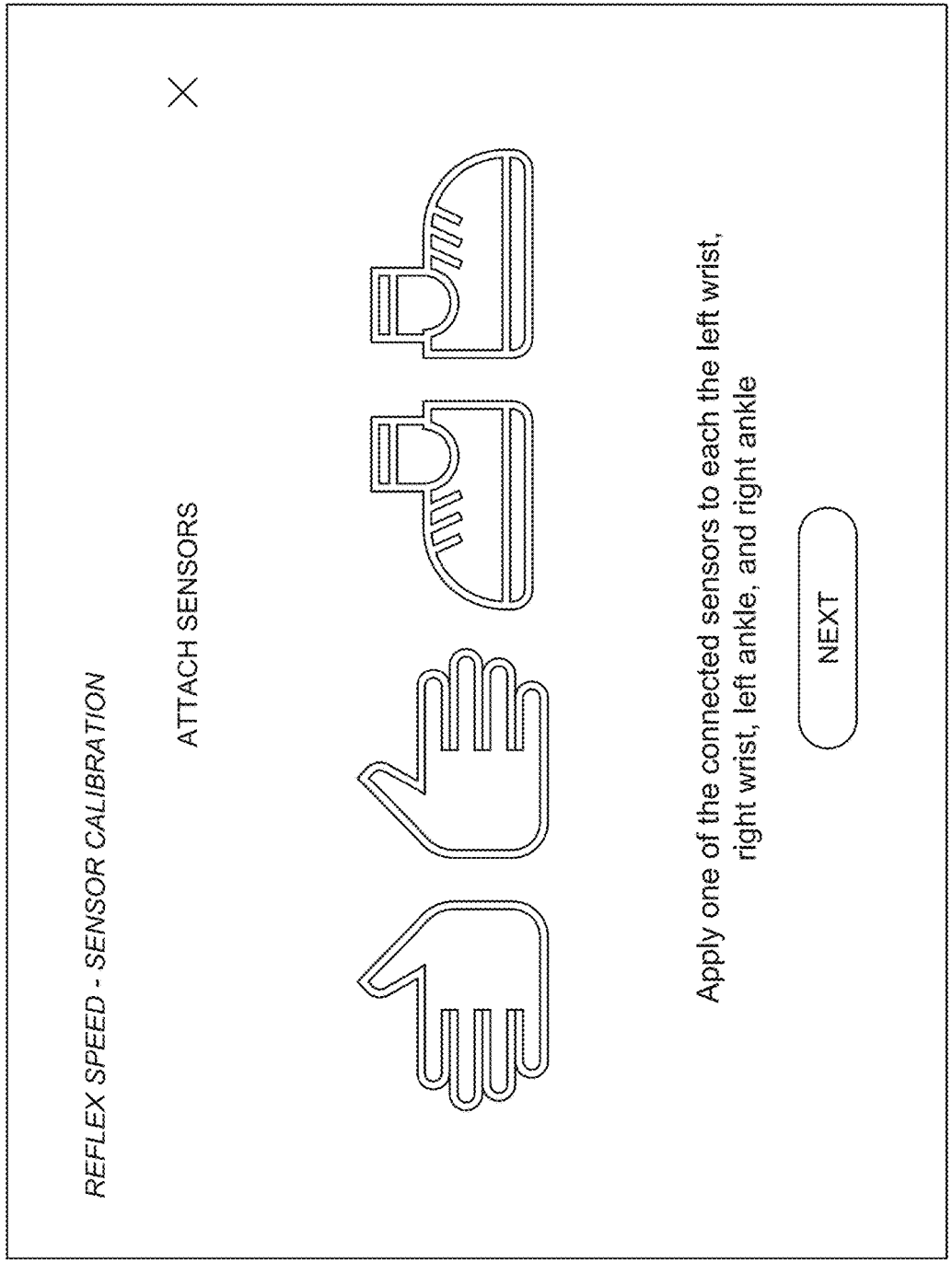
Figure 2E:
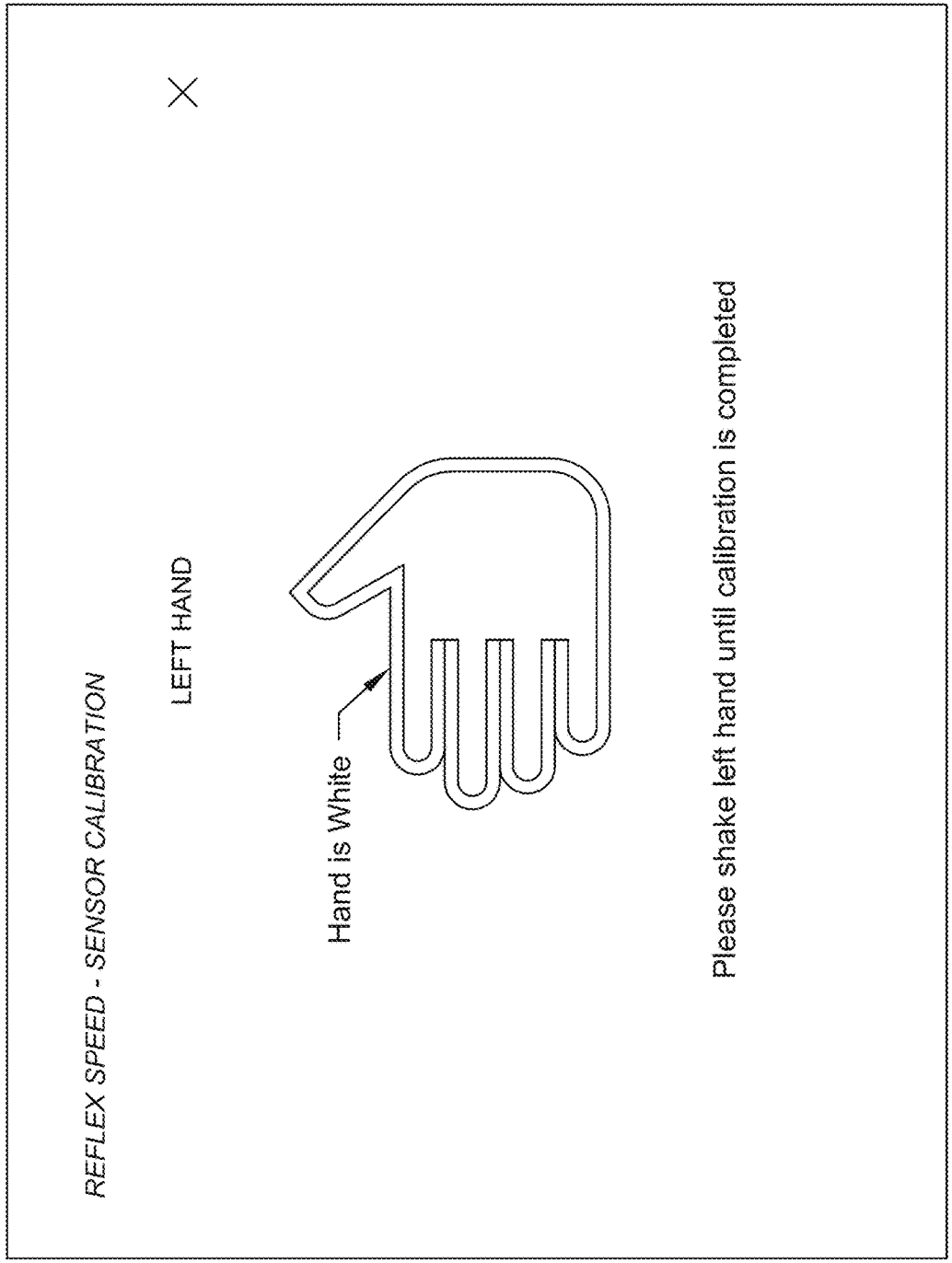
Figure 2F:
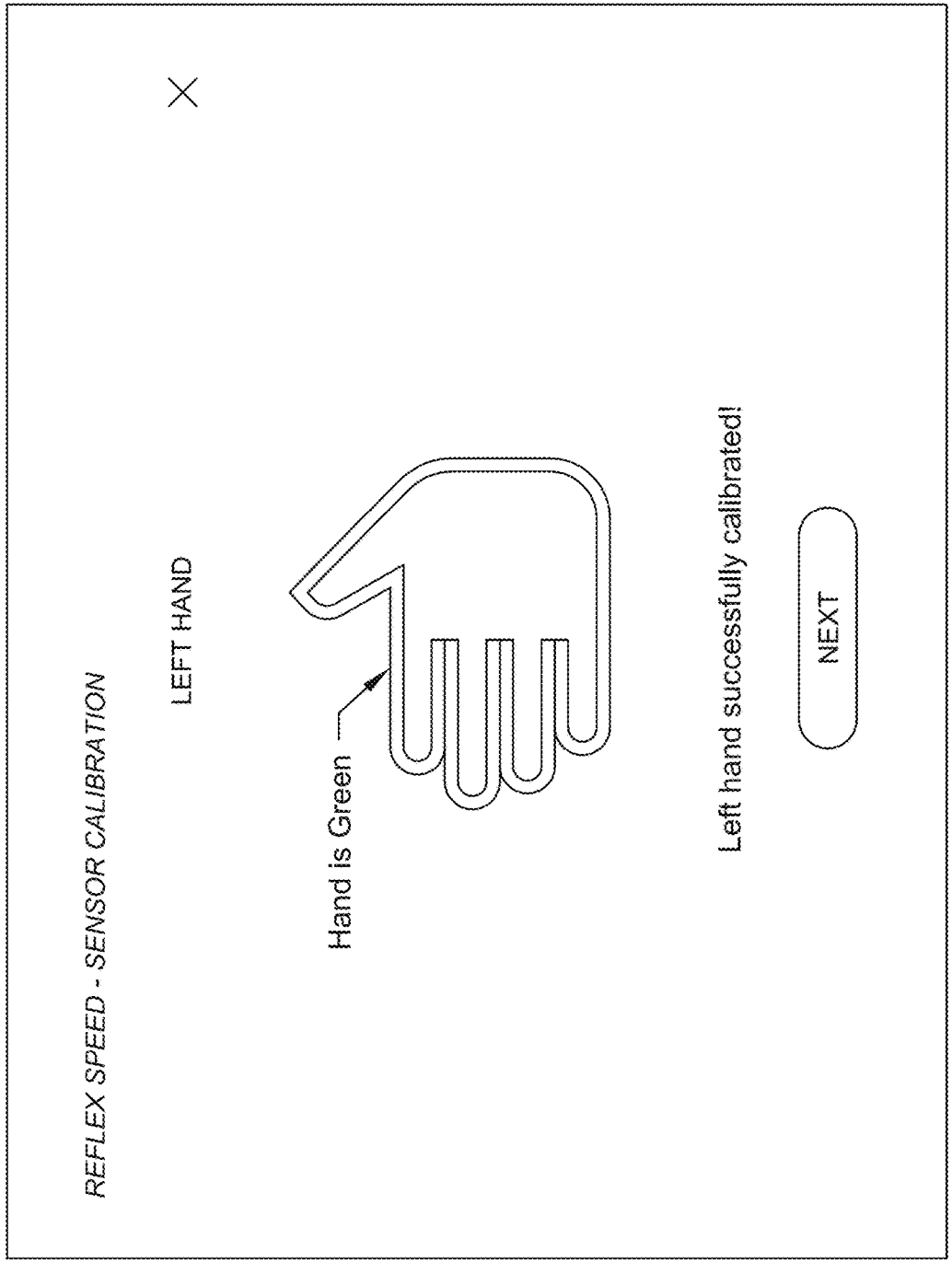
Figure 2G:
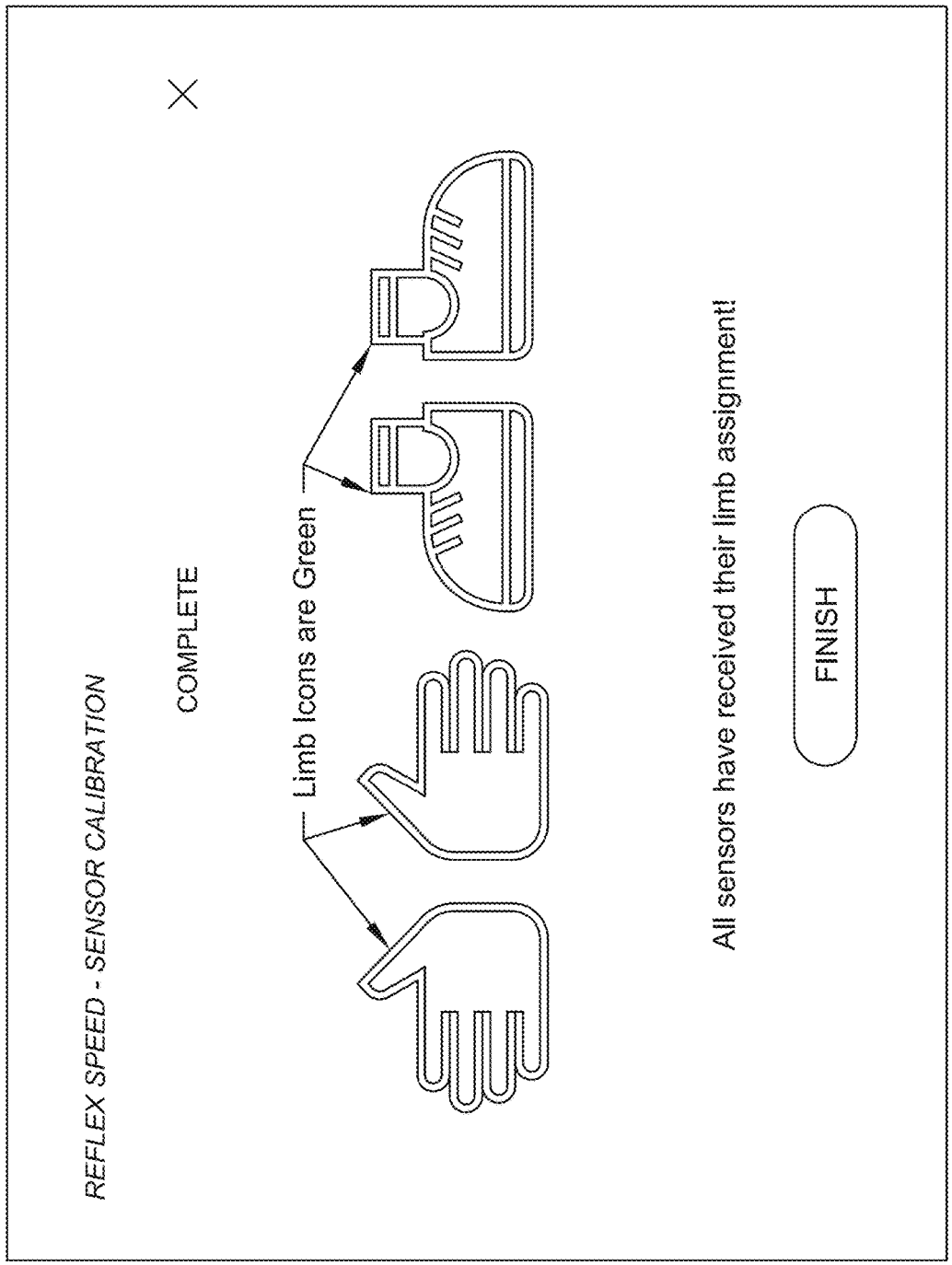
Figure 2I:
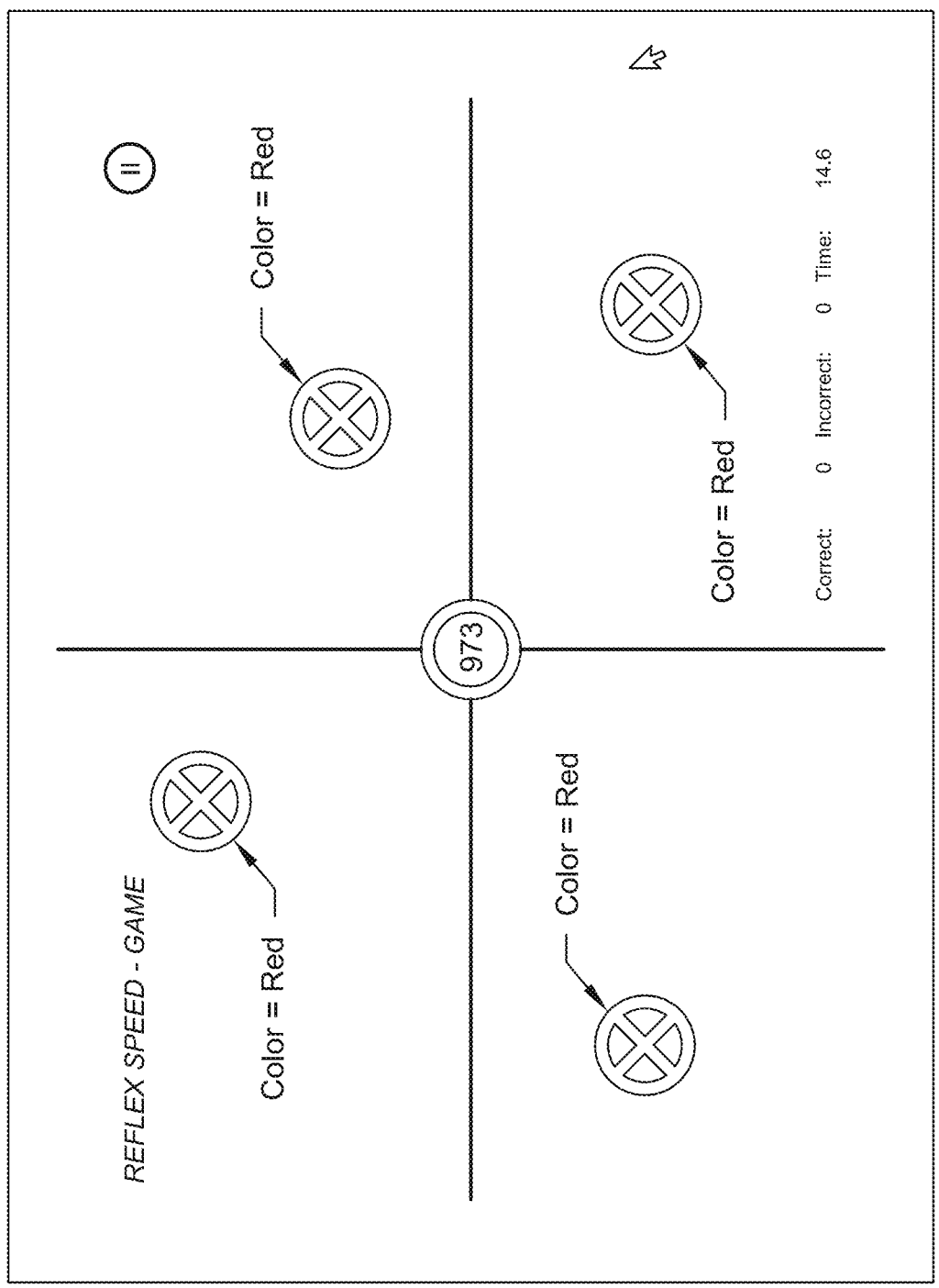
Figure 2J:
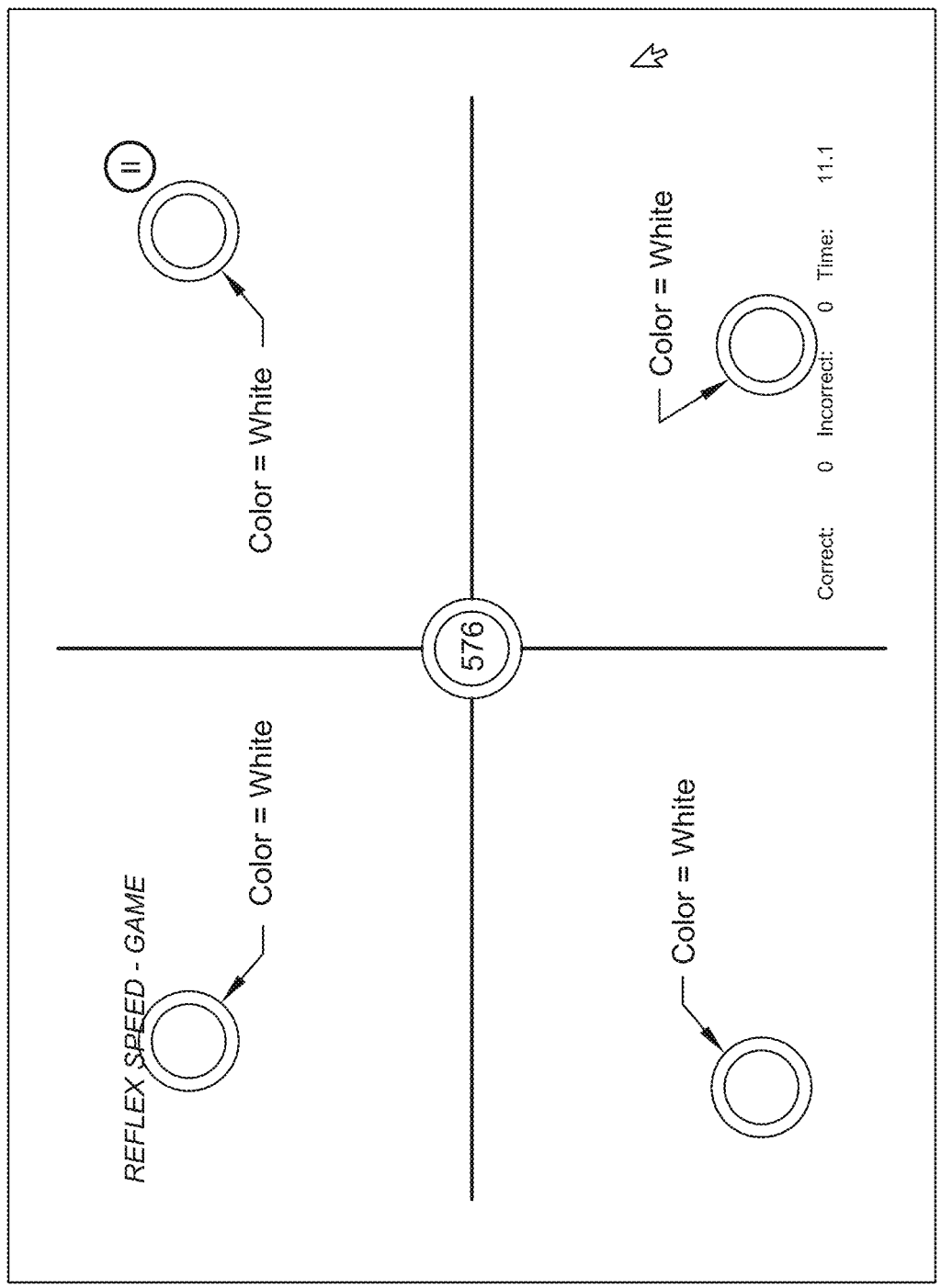
Figure 2K:
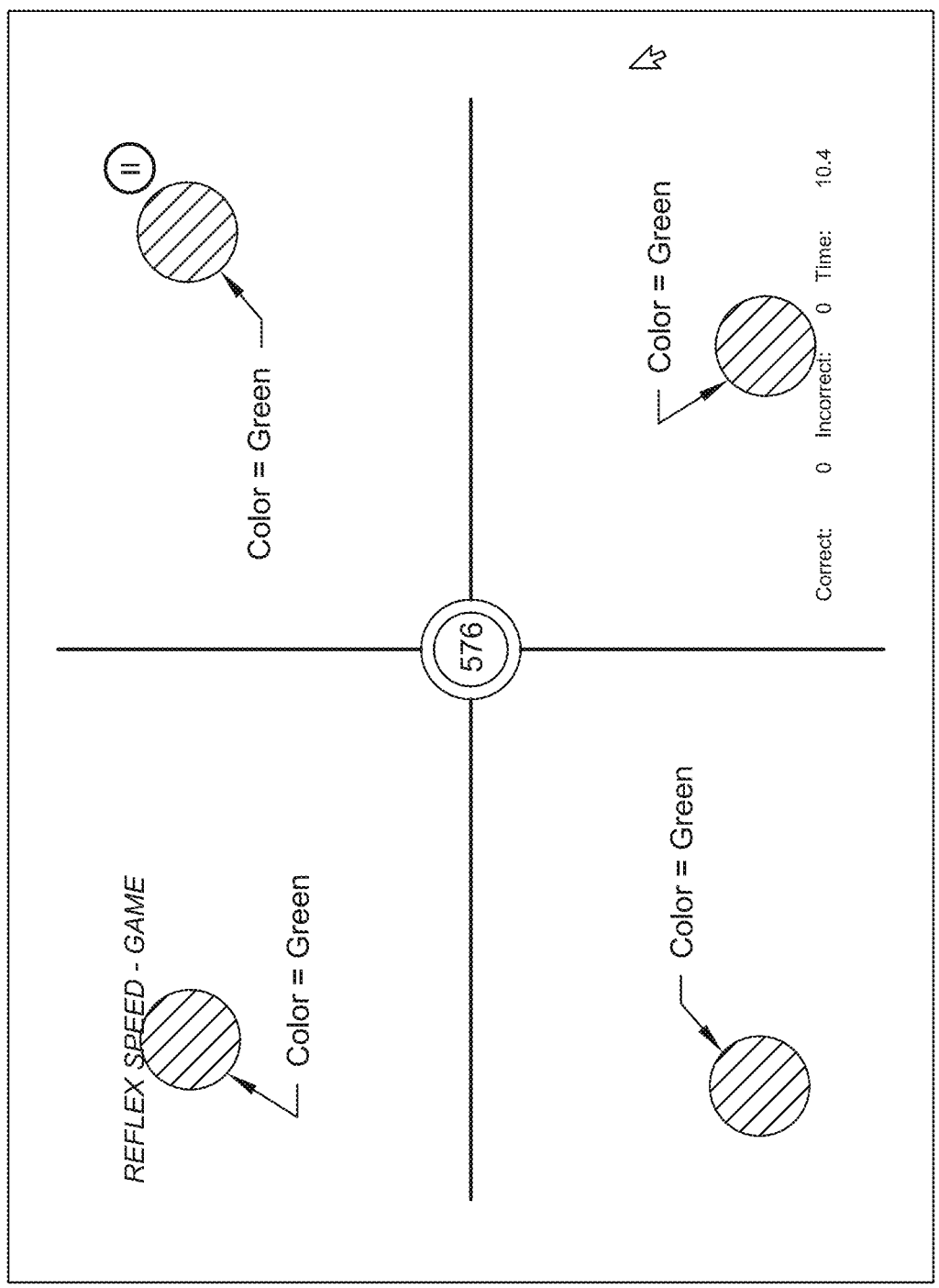
Figure 2L:
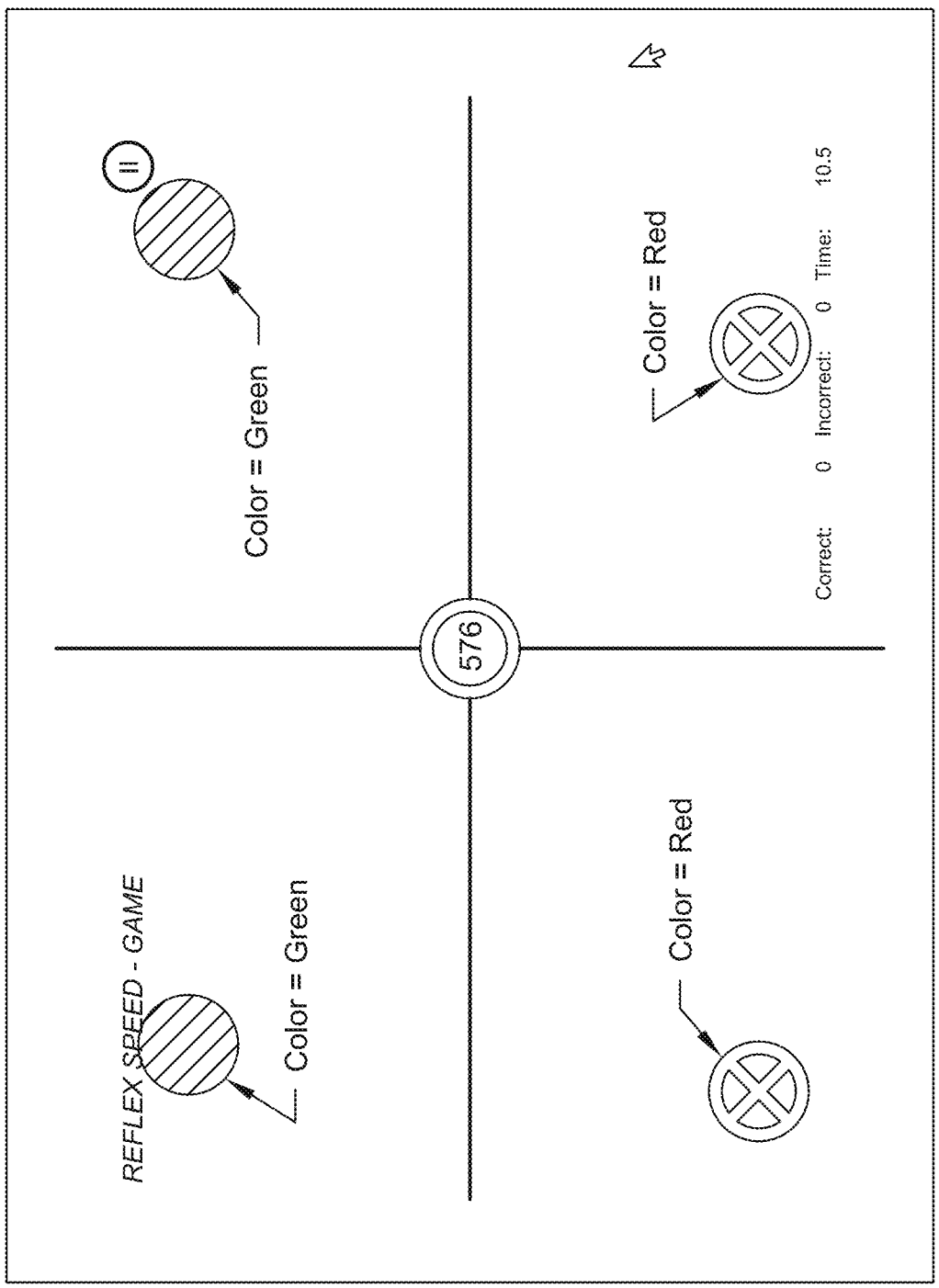
Figure 2M:
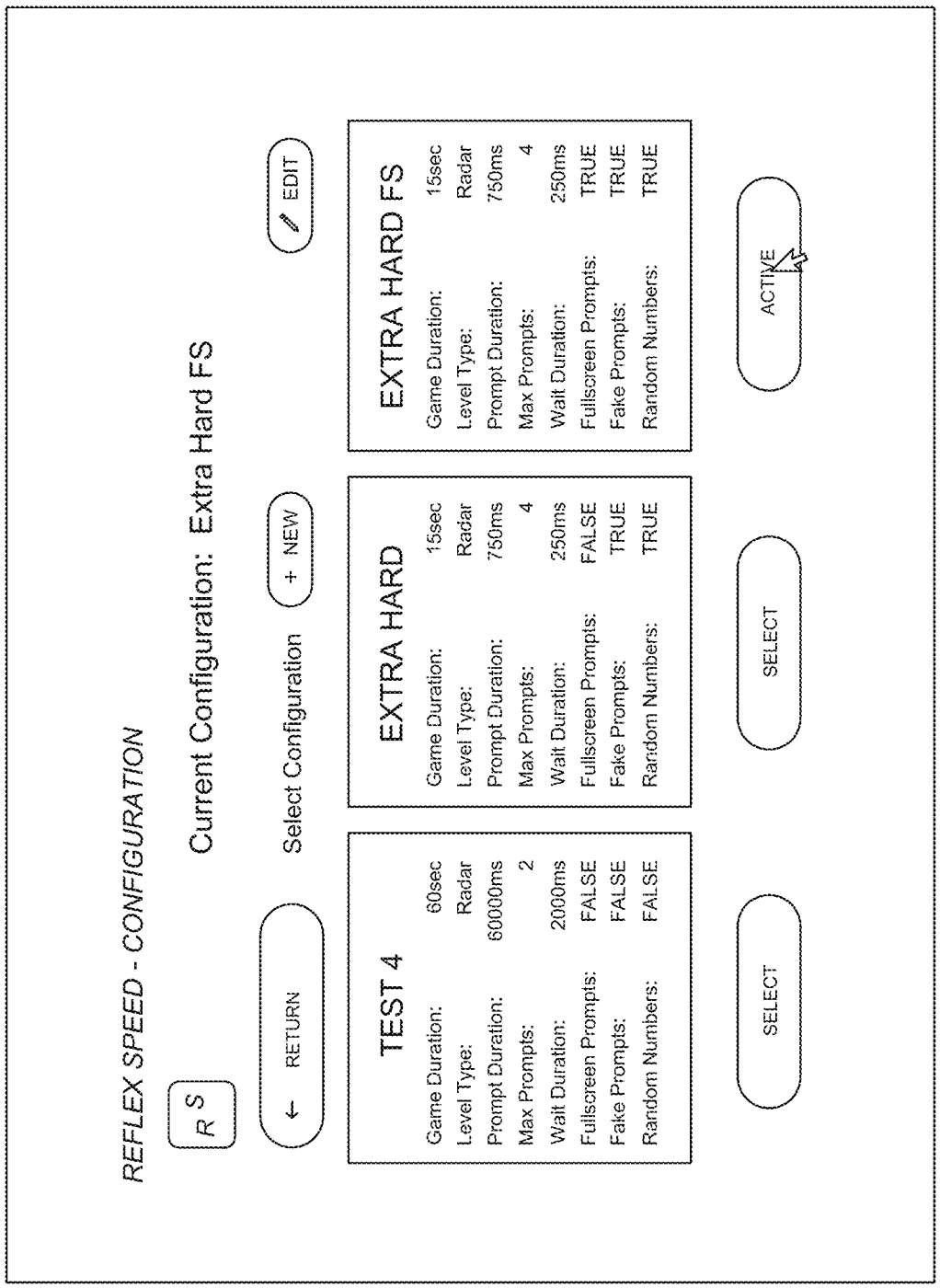
Figure 2N:
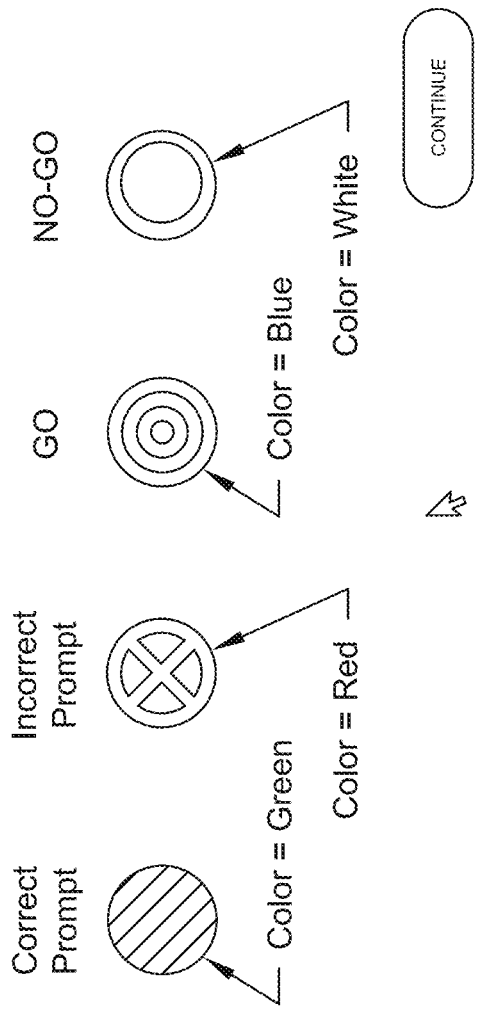

One example of pseudocode used to process data received from the motion tracking sensors and determine if a limb has made a responsive limb movement is provided below:

Algorithm Pseudocode
//Sensor device sends message to app device w/sensor data
//The acceleration data is collected from the sensor message, named accData: accData=sensorMessage.acc
//A vector of acceleration is collected from acceleration data, named vector: vector=accData.vectors[0]
//The magnitude of the acceleration from the motion recorded by the sensor is calculated: magnitude=sqrt((vector.x*vector.x)+(vector.y*vector.y)+(vector.z*vector.z))
//A baseline sensitivity is used for each limb, and each user is able to set their sensitivity level for each limb
//A threshold is determined by the user's sensitivity value or the baseline if not selected threshold=getUserLeftFootSensitivityThreshold( )?? baseLowerLimbSensitivityThreshold
//An action is determined by the following:
action=magnitude>threshold
//In the case where an action is observed, a message is sent to the session in progress
//At the beginning of the session, or after the previous instruction time duration
and the game session's configured wait duration have elapsed app device produces
instruction, displays it to the user, and records the starting time
instruction=generateInstruction( )
updateForNextInstruction(instruction)
instruction.startTime=Date( )
//At any point during the session, the user moves a limb
//Sensor device sends message to app device w/sensor data
//The acceleration data is collected from the sensor message, named accData:
accData=sensorMessage.acc
//A vector of acceleration is collected from acceleration data, named vector:
vector=accData.vectors[0]
//The magnitude of the acceleration from the motion recorded by the sensor is calculated:
magnitude=sqrt((vector.x*vector.x)+(vector.y*vector.y)+(vector.z*vector.z))
//A baseline sensitivity is used for each limb, and each user is able to set their sensitivity level for each limb
//A threshold is determined by the user's sensitivity value or the baseline if not selected
threshold=getUserLeftFootSensitivityThreshold( )?? baseLowerLimb SensitivityThreshold
//An action is determined by the following:
action=magnitude>threshold
//In the case where an action is observed, a message is sent to the session in progress
updateForAction(sensorMessage.limb, sensorMessage.timestamp)
//If action limb matches instruction limb and prompt duration has not expired,
record correctness and completion time
if limb==instruction.limb &&
    timestamp-instruction.startTime<instructionDuration
    instruction.isHit=true
    instruction.completionTime=Date( )
}
//Reaction speed can then later be calculated by
instruction.completionTime-instruction.startTime
End Algorithm Pseudocode FIGS. 2A-2N show user interface display screens for implementing preferred embodiments of the present invention.

FIG. 2A is the main landing screen after the user logs in. A variety of actions can be taken from this screen including sensor calibration and starting game sessions as described below.

FIGS. 2B-2G show the process for calibrating the sensors. The first step is for the user to wait for all four sensors to be detected (FIG. 2B). In FIG. 2C, two of the four sensors have been detected. After all four sensors have been detected, the user places each sensor on a different wrist or ankle (FIG. 2D) and proceeds through a succession of screens to associate each sensor with the appropriate limb. FIGS. 2E and 2F show that process for the left hand. FIG. 2G shows that the sensor association is complete.

FIGS. 2H-2K show an example of game play wherein max prompts=4. When a game is started, the user is shown the action that needs to be performed in each quadrant and is provided with a predetermined time window in which to react or not react, also referred to herein as the "measurement window." In the example of FIG. 2H, BLUE indicia means "GO" or "MOVE" and WHITE indicia means "NO-GO" or "DO NOT MOVE." If the action requested does not match the sensor measurement, the user is shown a RED indicia in the form of a RED "X" (e.g., FIG. 2I). If the action requested matches the sensor measurement, the user is shown GREEN indicia in the form of a GREEN circle (e.g., FIG. 2K).

FIG. 2N is a display screen that is preferably shown to the user prior to the display of the body movement instructions and summarizes the indicia that the user will see on the display screens. To summarize:
  GREEN=correct prompt
  RED=incorrect prompt
  BLUE=GO
  WHITE=NO-GO (as noted above, the lack of any indicia being displayed in a particular quadrant is equivalent to displaying NO-GO indicia in the particular quadrant)

In FIGS. 2H-2K, the colors are shown as target indicators or circle indicia (GREEN=green solid circle; RED=red hollow circle with an "x" inside of it; BLUE=two concentric blue hollow circles; WHITE=white hollow circle). However, other forms of indicia may be used such as full quadrant indicators or solid-colored rectangular indicia (e.g., solid green rectangle, solid red rectangle, solid blue rectangle, solid white rectangle). In addition, other embodiments may use other sets of distinguishable indicia or symbols. As long the user is trained on the meaning of the indicia, any type of indicia or symbols may be used.

Reaction times, correct responses and incorrect responses for each action are recorded and viewable on a leaderboard (not shown). More specifically, FIG. 2H shows a requested action (i.e., one human body movement instruction). FIG. 2I shows that the requested action did not match any of the sensor measurements. FIG. 2K shows that the requested action matched all of the sensor measurements. That is, all limbs responded appropriately by either moving or not moving as requested. FIG. 2L shows that two limbs responded appropriately, and two limbs did not.

FIG. 2M shows various configuration options including at least the following options:
  1. Game duration
  2. Level type ("Radar" refers to a game name/type)
  3. Prompt duration (this is equivalent to the "measurement window" discussed above)
  4. Max prompts 5. Wait duration (this is the time window between the end of the measurement window and the display of the next human body movement instruction which starts a new measurement window)

6. Fullscreen (Full-Screen) Prompts (ON or OFF, denoted by TRUE or FALSE)

7. Fake Prompts (ON or OFF, denoted by TRUE or FALSE. A fake prompt is a prompt that the person should not react to. Fake Prompts are thus equivalent to the "NO-GO" display feature described above.)

8. Random Numbers (ON or OFF, denoted by TRUE or FALSE. Referring to FIGS. 2H-2L, the center of the display screen optionally includes a circle where numbers can be displayed. In one embodiment, a random number may be displayed instead of a set number. The test subject is instructed to call out the number that they see.) This process provides additional cognitive load for the test subject because it requires engaging speech activity in the brain while simultaneously requiring the brain to make or not make motor (physical) movements. A microphone picks up audio signals from the test subject and then uses speech recognition technology determine if the correct number was spoken.

FIG. 3 shows a test setup with a user interface display screen and a human reacting to an action requested to be performed. Sensors are attached to the four limbs of the human as described above.

To summarize, while preferred embodiments of the present invention are directed to training a human body using contralateral movement, the display screens will not always show contralateral movement. Thus, part of the training process is to present both contralateral movement instructions and movement instructions that do not show contralateral movement. The training method described above is based on the scientific principle that the limb movement instructions themselves result in cognitive training of the brain.

Figure 4:
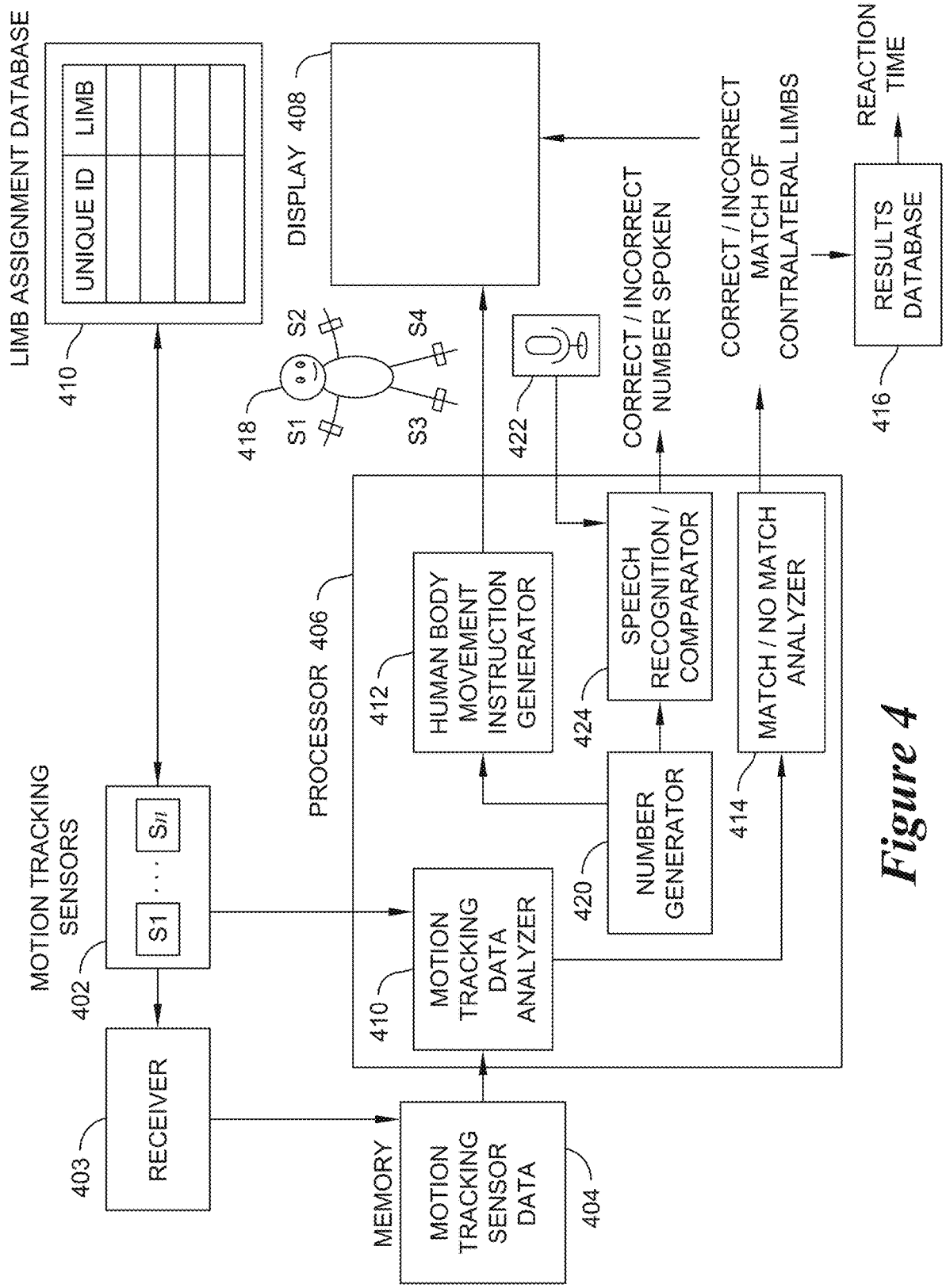
FIG. 4 is a schematic diagram of an apparatus for implementing one preferred embodiment of the present invention.

FIG. 4 is a schematic diagram of an apparatus (system) 400 for implementing one preferred embodiment of the present invention. The system 400 includes a plurality of motion tracking sensors 402, receiver 403, memory 404, processor 406, display 408, limb assignment database 410, and results database 416. The memory 404 stores data collected by the sensors 402. The processor 406 includes at least three modules as follows:

i. motion tracking data analyzer 410
ii. human body movement instruction generator 412
iii. match/no match analyzer 414

In operation, after the limb assignments are completed and stored in the limb assignment database 410, the human body movement instruction generator 412 presents the desired movement instruction on the display 408. Human 418 responds accordingly and limb sensors S1-Sn record any movement which are detected by the receiver 403. The movement data (motion tracking sensor data) is stored in the memory 404 and communicated to the processor 406. The motion tracking data analyzer 410 and the match/no match analyzer 414 process the sensor data to determine if the human 418 matched (correct match) or didn't match (incorrect match) the desired movement. This data populates the results database 416. Feedback may also be provided on the display 408 after each instruction to communicate to the human 418 whether the limbs made the appropriate response. The next instruction is then presented on the display 408. The process then repeats until the session is completed. The data in the results database 416 may also be used to calculate reaction time of the respective limbs.

If numbers are shown on the display 408, the system 400 further includes number generator 420 (which may be a random number generator), microphone 422 for sensing the human's voice, and speech recognition engine/comparator 424 for determining whether the person correctly spoke the number that appeared on the display 408. Similar to the limb movements, speech is only detected during the predetermined time window that the person has to react to the limb movement instructions.

IV. Other Considerations

1. Motion Tracking Sensor and Receiver

As discussed above, one suitable sensor is the Xsens DOT sensor. However, other inertial measurement unit (IMU) devices may be used. Any IMU may be used that has a form factor and durability suitable for the environment described herein. Another suitable IMU is the IMU described in U.S. Pat. No. 10,284,752 (Canfield et al.) which collects 9-degree of freedom (9-DOF) data, and which is incorporated herein by reference.

In one preferred embodiment, the receiver 403 is the Bluetooth® receiver of a mobile device (e.g., iPad®) that is used to implement parts of the system 400.

2. Alternatives to Display Screen

As discussed above, as long as the user is trained on the meaning of the indicia, any type of indicia or symbols may be used to prompt the user to make a specific body movement. Alternatively, other types of human-perceptible stimuli may be used to provide the prompts, such as sound (audio). Again, as long as the user is trained regarding what a particular sound means (e.g., sound A=move LH/RF, sound A=move LH/RH, sound B=move LH/LR/RH/RF, sound D=do not move any limbs, and so on), sound alone may provide the human body movement instructions.

3. Tracking Inhibition Control

Since the system described above can detect a condition when a specific limb moves but no movement instruction was given for the specific limb, the system can also track inhibition control of each limb. This information may be used for training purposes.

4. Use of Ipsilateral Movement Data

Preferred embodiments of the present invention focus on whether or not a person performs contralateral movements in accordance with instructions. However, since movement data is collected from all limbs, it may be possible to use the movement data for other purposes, such as detecting whether a user properly (correctly) responds to ipsilateral movement instructions (e.g., LH/LF, RH/RF), and if so, what the reaction times are. This information may be valuable for aiding with certain medical diagnoses such as stroke, partial paralysis, or dementia. Consider, for example, a person who responds correctly and within a normal (expected) reaction time period to LH/LF movement instructions, but fails to respond correctly to RH/RF movement instructions, or responds correctly to RH/RF movement instructions, but responds outside of a normal (expected) reaction time period. Such results may be indicative of a disease condition.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention.

What is claimed is:

1. An automated method for cognitive training of a brain of a human using contralateral movement, the body of the human (human body) being defined, in part, by having contralateral sides, wherein a plurality of motion tracking sensors are configured to be attached to limbs of the human body during the cognitive training of the brain of the human, at least two of the plurality of motion tracking sensors being connected to, and associated with, different contralateral limbs of the human body, the method comprising:
(a) displaying a succession of human body movement instructions outputted by a human body movement instruction generator on a display that is in view of the human, each human body movement instruction indicating different limbs of the human body that should be moved in response to the display, wherein at least some of the human body movement instructions indicate that contralateral limb movement should be made in response to the display, and wherein the contralateral limb movement is movement of limbs which are on opposite sides of the human body from one another;
(b) recording in memory of a processor a time of initial display of each of the human body movement instructions;
(c) recording limb movement of the plurality of motion tracking sensors, and detecting by the processor within a measurement window:
  (i) if or when the limb movement for each of the plurality of motion tracking sensors exceeds a predetermined threshold, thereby indicating a responsive limb movement, and
  (ii) a time when the limb movement for each of the plurality of motion tracking sensors exceeds the predetermined threshold; and
(d) for each of the succession of human body movement instructions which indicate that contralateral limb movement should be made in response to the display:
  (i) detecting by the processor whether any responsive limb movement occurred after the contralateral limb movement instructions were displayed using the recorded time of initial display of each of the human body movement instructions and the time when the limb movement for each of the plurality of motion tracking sensors exceeds the predetermined threshold; and
  (ii) recording in a database whether there is a correct or incorrect match of the contralateral limbs that should have been moved based on the contralateral limb movement instructions and the recorded time of initial display of each of the human body movement instructions and the time when the limb movement for each of the plurality of motion tracking sensors exceeds the predetermined threshold.

2. The method of claim 1 further comprising:
(e) calculating by the processor reaction time of the human to each of the contralateral limb movement instructions using the time of initial display of each of the human body movement instructions and a time that the limbs in the limb movement instructions are detected by the plurality of motion tracking sensors attached to the respective limbs as exceeding the predetermined threshold.

3. The method of claim 1 wherein the display includes four quadrants, one for each limb of the human body, and wherein each limb of the human body movement instruction is associated with a respective quadrant of the display.

4. The method of claim 1 wherein the human body movement instructions include directional movement instructions, and the plurality of motion tracking sensors include directional movement detection, wherein step (d)(i) further comprises detecting by the processor whether any responsive limb movement occurred with respect to the directional movement instructions, and
wherein step (d)(ii) further comprises recording whether there is a correct or incorrect match of the contralateral limbs that should have been moved based on the contralateral limb movement instructions with respect to the directional movement instructions.

5. An apparatus for cognitive training of a brain of a human using contralateral movement, the body of the human (human body) being defined, in part, by having contralateral sides, the apparatus comprising:
(a) a plurality of motion tracking sensors which are configured to be attached to limbs of the human body during the cognitive training of the brain of the human, at least two of the plurality of motion tracking sensors being connected to, and associated with, different contralateral limbs of the human body;
(b) a human body movement instruction generator configured to display a succession of human body movement instructions on a display that is in view of the human, each human body movement instruction indicating different limbs of the human body that should be moved in response to the display, wherein at least some of the human body movement instructions indicate that contralateral limb movement should be made in response to the display, and wherein the contralateral limb movement is movement of limbs which are on opposite sides of the human body from one another;
(c) memory configured to record a time of initial display of each of the human body movement instructions; and
(d) a processor configured to:
  (i) record limb movement of the plurality of motion tracking sensors, and detect by the within a measurement window:
    (A) if or when the limb movement for each of the plurality of motion tracking sensors exceeds a predetermined threshold, thereby indicating a responsive limb movement, and
    (B) a time when the limb movement for each of the plurality of motion tracking sensors exceeds the predetermined threshold; and
  (ii) for each of the succession of human body movement instructions which indicate that contralateral limb movement should be made in response to the display:
    (A) detect whether any responsive limb movement occurred after the contralateral limb movement instructions were displayed using the recorded time of initial display of each of the human body movement instructions and the time when the limb movement for each of the plurality of motion tracking sensors exceeds the predetermined threshold, and
    (B) record in a database whether there is a correct or incorrect match of the contralateral limbs that should have been moved based on the contralateral limb movement instructions and the recorded time of initial display of each of the human body movement instructions and the time when the limb movement for each of the plurality of motion tracking sensors exceeds the predetermined threshold.

6. The apparatus of claim 5 wherein the processor is further configured to:
(iii) calculate reaction time of the human to each of the contralateral limb movement instructions using the time of initial display of each of the human body movement instructions and a time that the limbs in the limb movement instructions are detected by the plurality of motion tracking sensors attached to the respective limbs as exceeding the predetermined threshold.

7. The apparatus of claim 5 wherein the display includes four quadrants, one for each limb of the human body, and wherein each limb of the human body movement instruction is associated with a respective quadrant of the display.

8. The apparatus of claim 5 wherein the human body movement instructions include directional movement instructions, and the plurality of motion tracking sensors include directional movement detection, wherein the processor is further configured to detecting whether any responsive limb movement occurred with respect to the directional movement instructions, and wherein the processor further records in the database whether there is a correct or incorrect match of the contralateral limbs that should have been moved based on the contralateral limb movement instructions with respect to the directional movement instructions.

* * * * *